United States Patent
Pierskalla et al.

(10) Patent No.: US 11,013,434 B2
(45) Date of Patent: May 25, 2021

(54) CARBON DIOXIDE SENSOR

(71) Applicant: EXOSTAT MEDICAL, INC., Prior Lake, MN (US)

(72) Inventors: Irvin T. Pierskalla, Prior Lake, MN (US); Kent R. Winger, Prior Lake, MN (US)

(73) Assignee: EXOSTAT MEDICAL, INC., Prior Lake, MN (US)

( * ) Notice: Subject to any disclaimer, the term of this patent is extended or adjusted under 35 U.S.C. 154(b) by 0 days.

(21) Appl. No.: 16/879,199

(22) Filed: May 20, 2020

(65) Prior Publication Data

US 2021/0109079 A1 Apr. 15, 2021

Related U.S. Application Data

(60) Provisional application No. 62/915,164, filed on Oct. 15, 2019.

(51) Int. Cl.
*A61B 5/145* (2006.01)
*G01N 33/483* (2006.01)
(Continued)

(52) U.S. Cl.
CPC ........ *A61B 5/14542* (2013.01); *A61B 5/1473* (2013.01); *A61B 5/14507* (2013.01); *A61B 5/682* (2013.01); *A61B 5/6847* (2013.01); *G01N 27/02* (2013.01); *G01N 33/004* (2013.01); *G01N 33/4836* (2013.01); *A61B 2560/0406* (2013.01);
(Continued)

(58) Field of Classification Search
CPC ... A61B 5/14542; A61B 5/682; A61B 5/6847; A61B 5/1473; A61B 5/14507; A61B 2560/0406; A61B 2562/168; A61B 2562/04; A61B 2562/02; G01N 33/004; G01N 27/02; G01N 33/4836
See application file for complete search history.

(56) References Cited

U.S. PATENT DOCUMENTS 4,207,160 A * 6/1980 Frankenberger ... A61B 5/14542
                                                    204/415
5,763,762 A * 6/1998 Sweeney, Jr. ............ G01N 7/10
                                                    73/19.05
(Continued)

OTHER PUBLICATIONS

Lu et al. "A High Precision, Fast Response, and Low Power Consumption in situ Optical Fiber Chemical pCO2 Sensor." Talanta. Jul. 15, 2008;76(2):353-9. (Year: 2008).*

(Continued)

*Primary Examiner* — Meredith Weare
(74) *Attorney, Agent, or Firm* — Fox Rothschild LLP

(57) ABSTRACT

A physiologic sensor for measuring the partial pressure of carbon dioxide is provided. The sensor includes a generally C-shaped in cross-section sensor cover, the sensor cover defining an opening on an underside thereof; a membrane body housed within the opening, the membrane comprising an amorphous fluoroplastic, the membrane including a first end and a second end and defines a chamber therewithin; a sensor body for coupling the membrane to the sensor cover; two or more electrodes positioned within the membrane chamber; and a substantially electrolyte-free liquid contained within the membrane chamber and in contact with the two or more electrodes.

10 Claims, 5 Drawing Sheets

(51) Int. Cl.
*G01N 27/02* (2006.01)
*G01N 33/00* (2006.01)
*A61B 5/1473* (2006.01)
*A61B 5/00* (2006.01)

(52) U.S. Cl.
CPC ....... *A61B 2562/02* (2013.01); *A61B 2562/04* (2013.01); *A61B 2562/168* (2013.01)

(56) References Cited

U.S. PATENT DOCUMENTS

| | | | |
|---|---|---|---|
| 6,068,743 A * | 5/2000 | Fleckenstein | A61B 5/14542 204/402 |
| 7,811,433 B2 | 10/2010 | Manoukian et al. | |
| 8,996,090 B2 * | 3/2015 | Anderson | A61B 5/14546 600/345 |
| 2002/0087057 A1 * | 7/2002 | Lovejoy | A61B 5/4238 600/349 |
| 2002/0168296 A1 | 11/2002 | Gambert | |
| 2003/0178304 A1 * | 9/2003 | Tonnessen | G01N 33/4925 204/431 |
| 2004/0003714 A1 | 1/2004 | Bikson et al. | |
| 2004/0006263 A1 * | 1/2004 | Anderson | A61B 5/1459 600/364 |
| 2005/0203362 A1 * | 9/2005 | Castillo | A61B 5/682 600/353 |
| 2007/0142717 A1 * | 6/2007 | Lowery | A61B 5/14552 600/323 |
| 2008/0011615 A1 * | 1/2008 | Omtveit | G01N 33/4925 205/777 |
| 2008/0039703 A1 * | 2/2008 | Omtveit | A61B 5/1473 600/353 |
| 2008/0319278 A1 | 12/2008 | Omtveit et al. | |
| 2010/0044226 A1 | 2/2010 | Tonnessen et al. | |
| 2012/0271131 A1 | 10/2012 | Kling et al. | |
| 2013/0197332 A1 * | 8/2013 | Lucisano | A61B 5/14532 600/345 |
| 2013/0274575 A1 * | 10/2013 | Winger | A61B 5/1495 600/353 |
| 2016/0220833 A1 * | 8/2016 | Tan | G09B 19/003 |

OTHER PUBLICATIONS

PCT International Search Report and Written Opinion dated Jul. 29, 2020, for application No. PCT/US2020/033779, 15 pages.

* cited by examiner

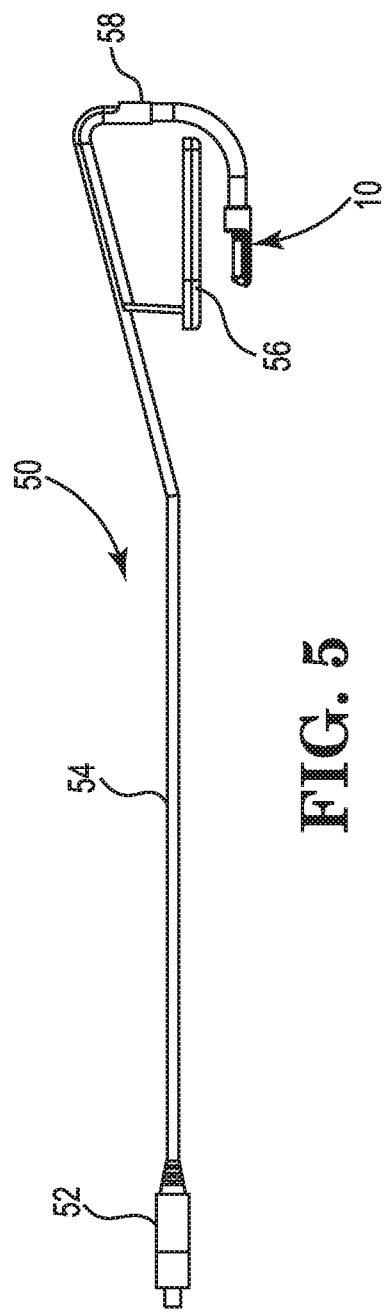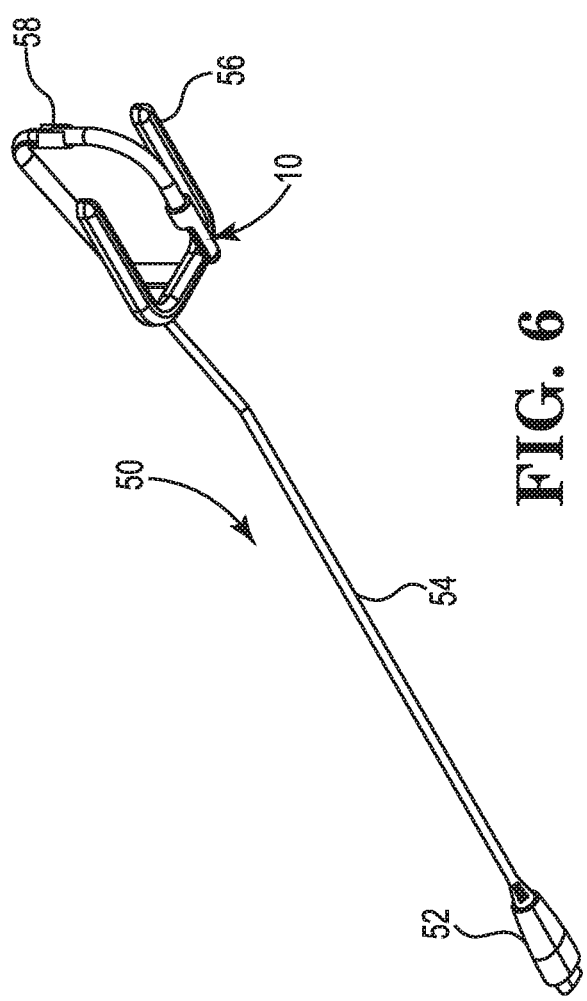

CARBON DIOXIDE SENSOR

CROSS REFERENCE TO RELATED APPLICATION(S)

This application claims benefit to Provisional Application No. 62/915,164, filed on Oct. 15, 2019. The contents of which are incorporated herein by reference.

FIELD OF THE INVENTION

The invention relates to the field of sensors for measuring the partial pressure of carbon dioxide ($pCO_2$) in tissue. More particularly, the invention relates to sensors for measuring the partial pressure of carbon dioxide in mucosal tissue.

BACKGROUND OF THE INVENTION

Very low blood flow, known as hypoperfusion can be caused by low blood volume, inadequate pumping action of the heart, or excessive widening (dilation) of blood vessels.

The body responds to such stress by reducing blood flow to less critical organs, such as the gastrointestinal tract, to spare blood for other, more critical organs. Thus, when there is a reduced flow of blood from the heart, the body directs a higher portion of blood to critical organs, such as the brain, which will not survive long without a continuous supply of blood, while restricting the flow of blood to less critical organs, whose survival is not as threatened by a temporary large reduction in blood flow.

For example, blood flow to the splanchnic vasculature, which supplies the stomach and intestines, and blood flow to the esophagus and oral/nasal cavity, is drastically reduced when there is reduced blood flow from the heart. For this reason, decreased blood flow to the splanchnic blood vessels is an indication of hypoperfusion in a patient. When hypoperfusion compromises intestinal mucosa, ischemia and gastric hypercapnia follow. These two clinical states can spur the release of bacteria and inflammatory substances into the splanchnic circulation, leading to sepsis and multiple organ dysfunction syndrome.

Carbon dioxide production, which is associated with metabolism, continues in tissues even during conditions of low blood flow. The concentration of carbon dioxide builds-up in tissues experiencing low blood flow because carbon dioxide is not rapidly carried away. This carbon dioxide build-up is exhibited by an increase in $pCO_2$ in organs. Therefore, hypoperfusion is commonly assessed by measuring $pCO_2$ at these sites.

Increases in $pCO_2$ may be measured throughout the body. Particularly, studies have shown that oral mucosal $pCO_2$ correlates well with gastric $pCO_2$ and thus oral mucosal constitutes an ideal site to measure $pCO_2$, especially if the sensing probe is isolated from ambient air and can be seated in a patient's mouth with minimal discomfort. Numerous studies have documented that both sublingual and buccal mucosal $pCO_2$ levels track circulatory stress in a quantitative fashion.

Measurements of $pCO_2$ have traditionally been taken with sensors having silicone membranes. Silicone membranes are useful because the large free volume in the polymer chain allows for rapid gas transport. Disadvantageously, however, silicone membranes also allow carboxylic acids, such as acetic acid, and other compounds found in saliva to pass through as well, which can interfere with $pCO_2$ measurements. For example, when acetic acid crosses the membrane into the sensor fluid, the pH is lowered and the conductivity of the fluid increases. Both alterations may falsely indicate an increase in carbon dioxide.

Therefore, what is needed is a new design that allows for the rapid transmission of carbon dioxide while preventing the transmission of low molecular weight acids found in the saliva.

BRIEF SUMMARY OF THE INVENTION

The foregoing problems are addressed by the carbon dioxide sensor in accordance with the invention.

In one aspect, the sensor includes a generally C-shaped in cross-section sensor cover, the sensor cover defining an opening on an underside thereof; a membrane body housed within the opening, the membrane body comprising an amorphous fluoroplastic, the membrane body including a first end and a second end and defining a chamber therewithin; a sensor body for coupling the membrane body to the sensor cover; two or more electrodes positioned within the membrane body; and a substantially electrolyte-free liquid contained within the membrane body chamber and surrounding the two or more electrodes.

These and other aspects of the invention will be disclosed in the Detailed Description and appended claims.

BRIEF DESCRIPTION OF THE DRAWINGS

For a better understanding of the invention, and to show how the same may be carried into effect, reference will now be made, by way of example, to the accompanying drawings, in which:

FIG. 5 is a side view of a sensor placement device for positioning the carbon dioxide sensor against a buccal surface.

FIG. 6 is a perspective view of the sensor placement device for positioning the carbon dioxide sensor against a buccal surface.

DETAILED DESCRIPTION OF THE INVENTION

Figure 2:
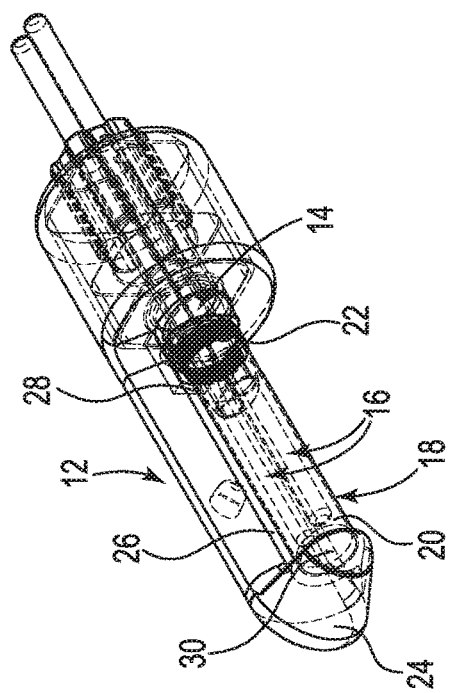
FIG. 2 is a perspective view of the carbon dioxide sensor in accordance with the invention.
Figure 4:
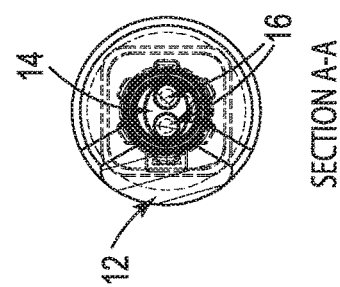
FIG. 4 is a cross-sectional view of the carbon dioxide sensor in accordance with the invention taken along line A-A of FIG. 3.

In the drawings, like reference numerals designate identical or corresponding parts throughout the several views.

As used herein, the words "a," "an" and the like generally carry a meaning of "one or more," unless stated otherwise. The term "plurality", as used herein, is defined as two or more than two. The term "another", as used herein, is defined as at least a second or more. The terms "including" and/or "having", as used herein, are defined as comprising (i.e., open language).

Reference throughout this document to "one embodiment", "certain embodiments", "an embodiment", "an implementation", "an example" or similar terms means that a particular feature, structure, or characteristic described in connection with the example is included in at least one example of the present disclosure. Thus, the appearances of such phrases or in various places throughout this specification are not necessarily all referring to the same example. Furthermore, the particular features, structures, or characteristics may be combined in any suitable manner in one or more examples without limitation.

The term "or" as used herein is to be interpreted as an inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

Further, in individual figures, some components/features shown are drawn to scale to exemplify a particular implementation while other components and features are not drawn to scale.

Figure 1:
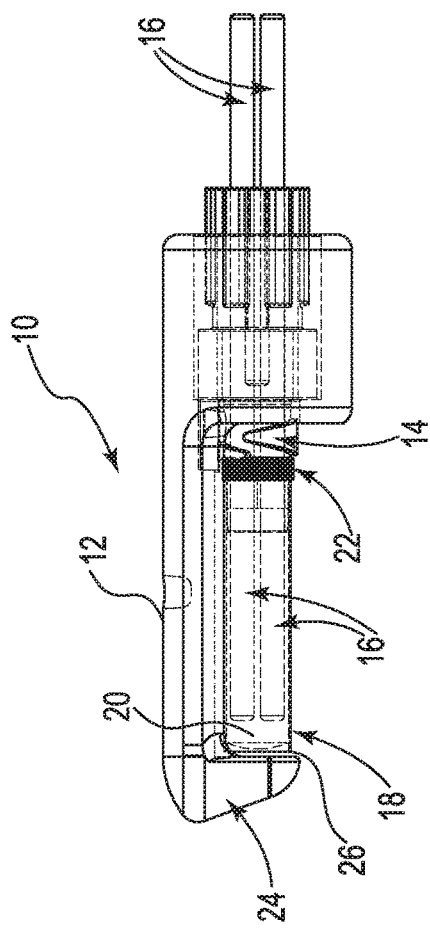
FIG. 1 is a side view of the carbon dioxide sensor in accordance with the invention.
Figure 3:
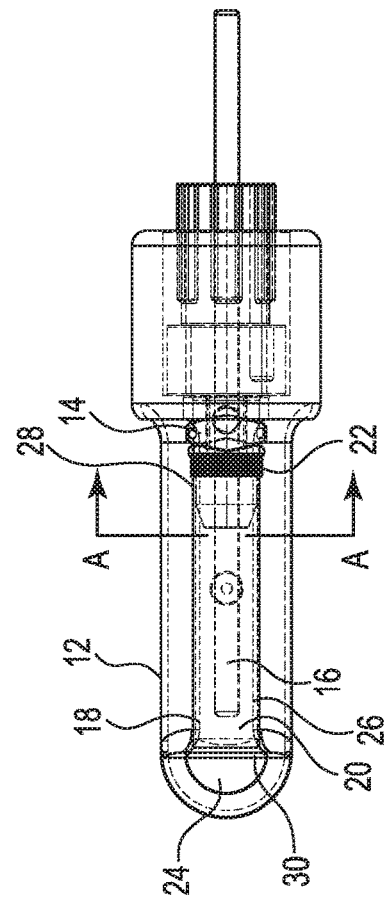
FIG. 3 is a bottom view of the carbon dioxide sensor in accordance with the invention.

Referring now to FIG. 1 a side view of the carbon dioxide sensor in accordance with the invention is shown. The sensor 10 broadly includes sensor cover 12, sensor body 14, pair of electrodes 16, membrane body 18, sensor fluid 20 and winding filament 22.

The sensor cover may be constructed of a thermoplastic such as polyethylene, polypropylene, polystyrene and polycarbonate. The sensor cover 12 generally covers and houses the sensor body 14 and membrane body 18. Sensor cover 12 is shaped such that it forms an opening 26 on an underside thereof for housing the sensor body 14 and membrane body 18. One such shape is a generally C-shaped in cross section. Those of skill in the art will appreciate however that other shapes are also suitable such as D-shaped, semi-circular, elliptical and the like. Sensor cover 12 includes a downwardly projecting lip 24 that shields the membrane body 18 from end tidal carbon dioxide when in use. Advantageously, the sensor cover 12 permits tissue contact for greater than 40% to 50% of membrane body 18.

Sensor body 14 may also be constructed of a thermoplastic such as polyethylene, polypropylene, polystyrene and polycarbonate. Sensor body 14 may be constructed of the same thermoplastic as sensor cover 12 or may comprise a different thermoplastic. Preferably, for manufacturing cost efficiencies sensor body 14 is constructed of the same thermoplastic as sensor cover 12. Sensor body 14 is configured to hold and align electrodes 16 securely in place within membrane body 18. Sensor body 14 provides an attachment point for membrane body 18 and for securing the winding filament 22 to provide a secure attachment between the sensor body and the membrane body 18. Those of skill in the art will appreciate that other attachments may be used such as snap-on, adhesives, bonding and crimping.

Pair of electrodes 16 are constructed of stainless steel and are configured to receive an alternating electrical potential from a supply source. Those of skill in the art will appreciate that metals other than stainless steel may also be used. Electrodes 16 are positioned securely in place by sensor body 14. Electrodes 16 are housed within membrane body 18 and positioned in sensor fluid 20. Those of skill in the art will appreciate that two or more electrodes may be used and still fall within the scope of the invention. For example, conductance can be measured with two, three, or four electrodes.

Membrane body 18 is positioned in opening 26 of sensor cover 12. Membrane body 18 comprises a hollow tube defining a chamber therewithin. The membrane body 18 is substantially impermeable to low molecular weight carboxylic acids, including acetic acid, which is found in *salvia* and can compromise precise readings of carbon dioxide levels in oral mucosa. Membrane body 18 may be constructed of fluoropolymer resins such as an amorphous fluoroplastic. Suitable amorphous fluoroplastics include Teflon AF 2400 (available from The Chemours Company). Teflon AF 2400 is known to have exceptional permeability for carbon dioxide. However, heretofore, it has been undiscovered that amorphous fluoroplastics, such as Teflon AF 2400, have a structure with a large free volume in the polymer chain that allows for rapid carbon dioxide transport but also does not permit carboxylic acids, such as acetic acid, to transport across it. Teflon AF 2400 has a carbon dioxide permeability of 2800 Barrer units as compared to polytetrafluoroethylene which has a carbon dioxide permeability of 120 Barrer units. Alternatively, polymethylpentenes (available from Mitsui Chemicals America) may be used in place of an amorphous fluoroplastic. Membrane body 18 is open at a first end 28 to allow for filling with sensor fluid 20 prior to attachment to the sensor body 14, which then seals it. A second end 30 is sealed with Teflon AF 1600, which has a much lower carbon dioxide transmission rate than AF 2400. Teflon AF 1600 easily fuses to membrane body 18 and provides a leak free environment. The second end of the tube is situated against lip 24 so it does not contact tissue and does not need to be permeable to carbon dioxide. Sensor fluid 20 may be a substantially electrolyte-free liquid such as pharmaceutical-grade purified water (USP grade water). In some aspects of the invention distilled water may also be used.

Winding filament 22 is used to secure the membrane body 18 to sensor body 12. Adhesive may be used to bond and reinforce the winding filament 22.

Figure 7:
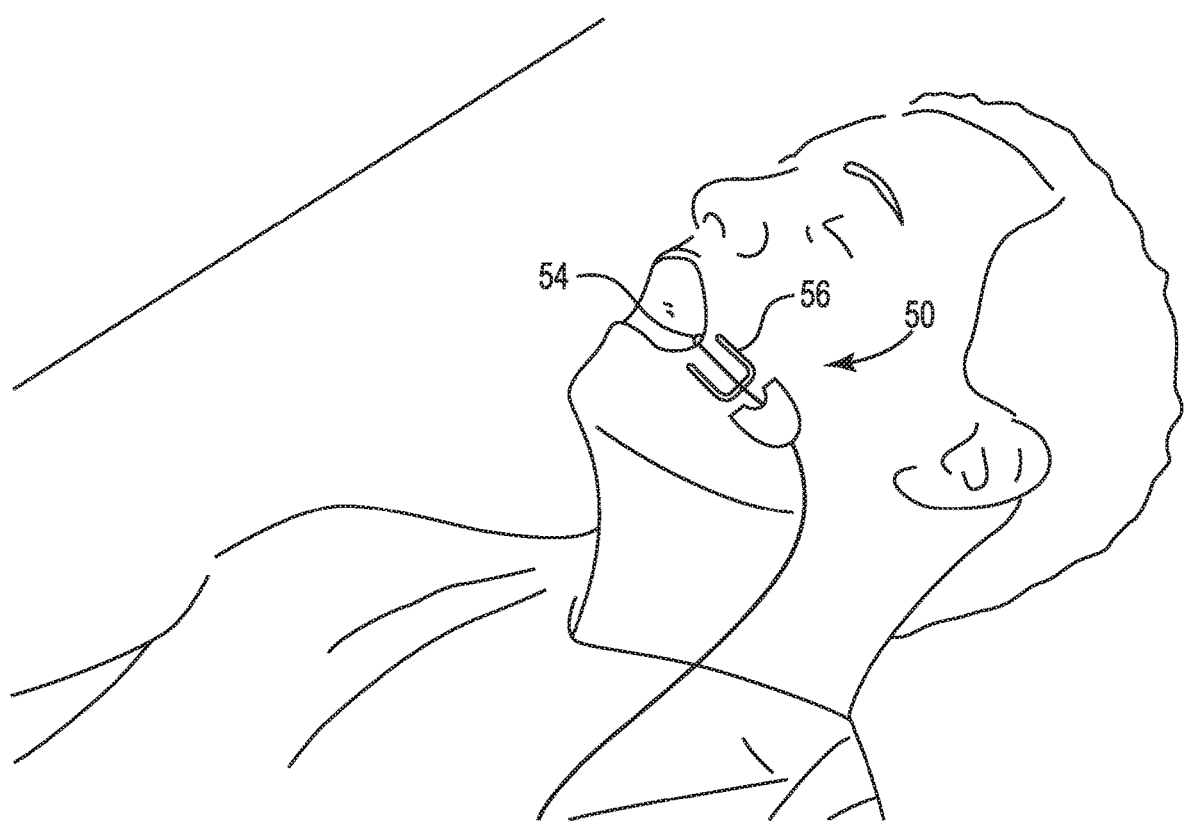
FIG. 7 is a perspective view of the sensor placement device being used on a patient.

Referring now to FIGS. 5-7 a sensor placement device 50 for secure placement of the sensor 10 against a buccal surface is illustrated. The sensor placement device broadly includes proximal end 52, elongate middle portion 54 and distal end 56. Proximal end 52 is adapted to operably couple to electronics for reading and displaying the $pCO_2$ measurements. Distal end 56 includes U-shaped portion 56 for positioning the device 50 against the outside surface of the cheek and the sensor on the inside of the cheek. Sensor 10 is attached to the positioning device 50 by arm 58.

In operation to be used to measure tissue $pCO_2$ in the oral cavity, the sensor 10 is deployed in a sensor placement device 50 configured to fit the human cheek. As shown, sensor placement device 50 with sensor 10 is a disposable device. Using the elongate middle portion, a user inserts the sensor 10 into the mouth and positions U-shaped portion 56 to the outside surface of the cheek. This, in turn, holds the sensor 10 against the buccal surface of the cheek. The device 50 is designed so the sensor 10 is held in direct contact with the buccal tissue without air gaps and without applying pressure in excess of 25 mmHg and preferably less than 15 mmHg. Excess pressure can disturb blood flow and alter the level of $pCO_2$.

Sensor cabling (not shown) attaches the sensor placement device with sensor to electronic equipment (not shown) that provides an alternating electrical potential to the sensor 10 and measures the impedance of the sensor fluid 20 contained within membrane body 18. The equipment is calibrated to the sensor response curve and an algorithm calculates the $pCO_2$ value from the temperature-adjusted conductance signal. The sensor response curve is determined by measuring the sensor signal in two reference solutions of known $pCO_2$ levels; a low $pCO_2$ reference and a "normal" $pCO_2$ reference. The "normal" solution approximates the $pCO_2$ of healthy, well perfused tissue. From this data, the slope of the response curve is determined. Values of $pCO_2$ are then calculated from the signal difference from the "normal" reference solution. The calculated $pCO_2$ values are then displayed graphically and numerically on an integrated display. The electronic device is configured as a standalone patient monitoring device, but those of skill in the art will appreciate that it can be integrated into a multi-modal patient monitoring system.

Figure 8:
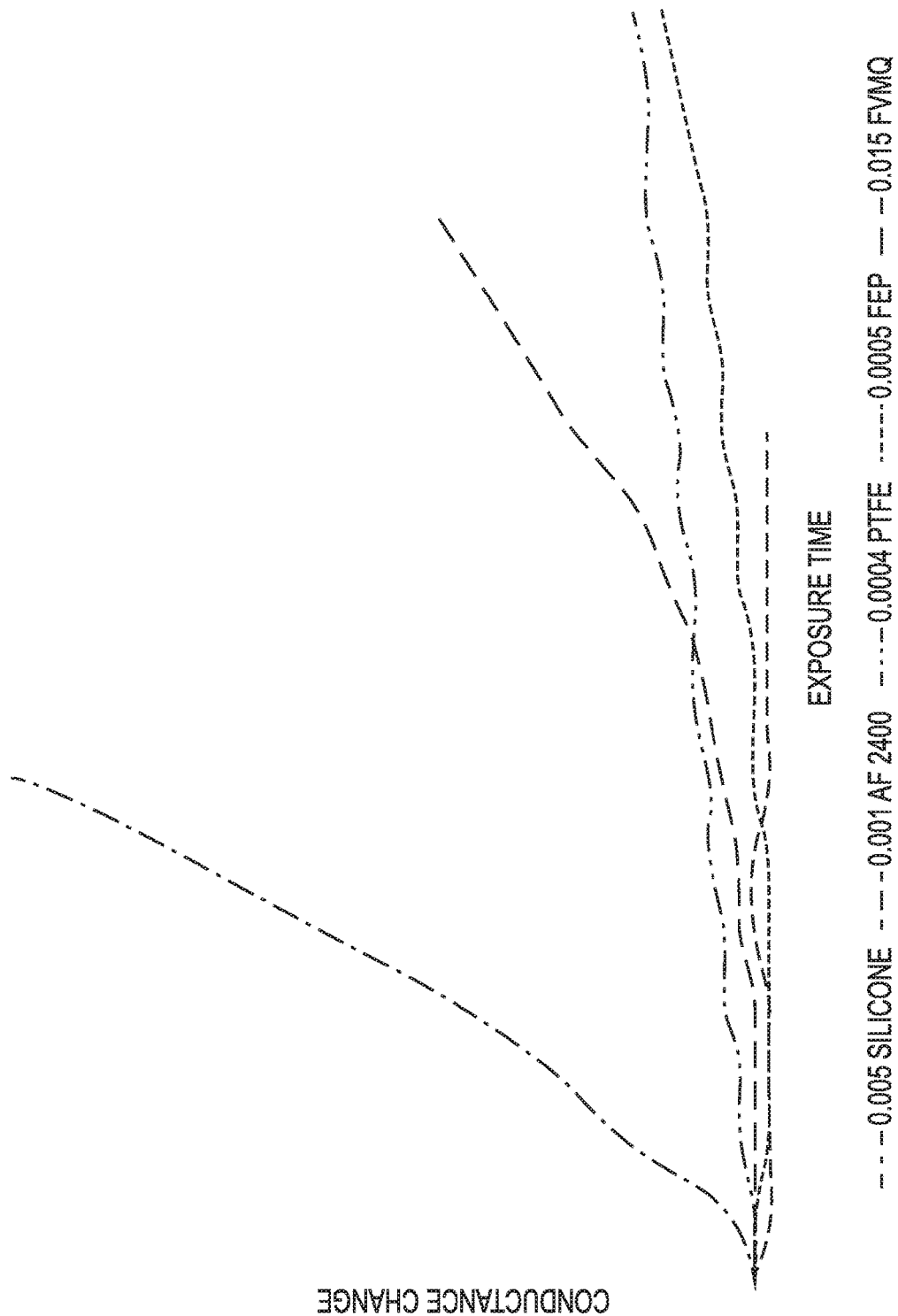
FIG. 8 is a graph illustrating a comparison of various membrane materials exposure to acetic acid.
Figure 9:
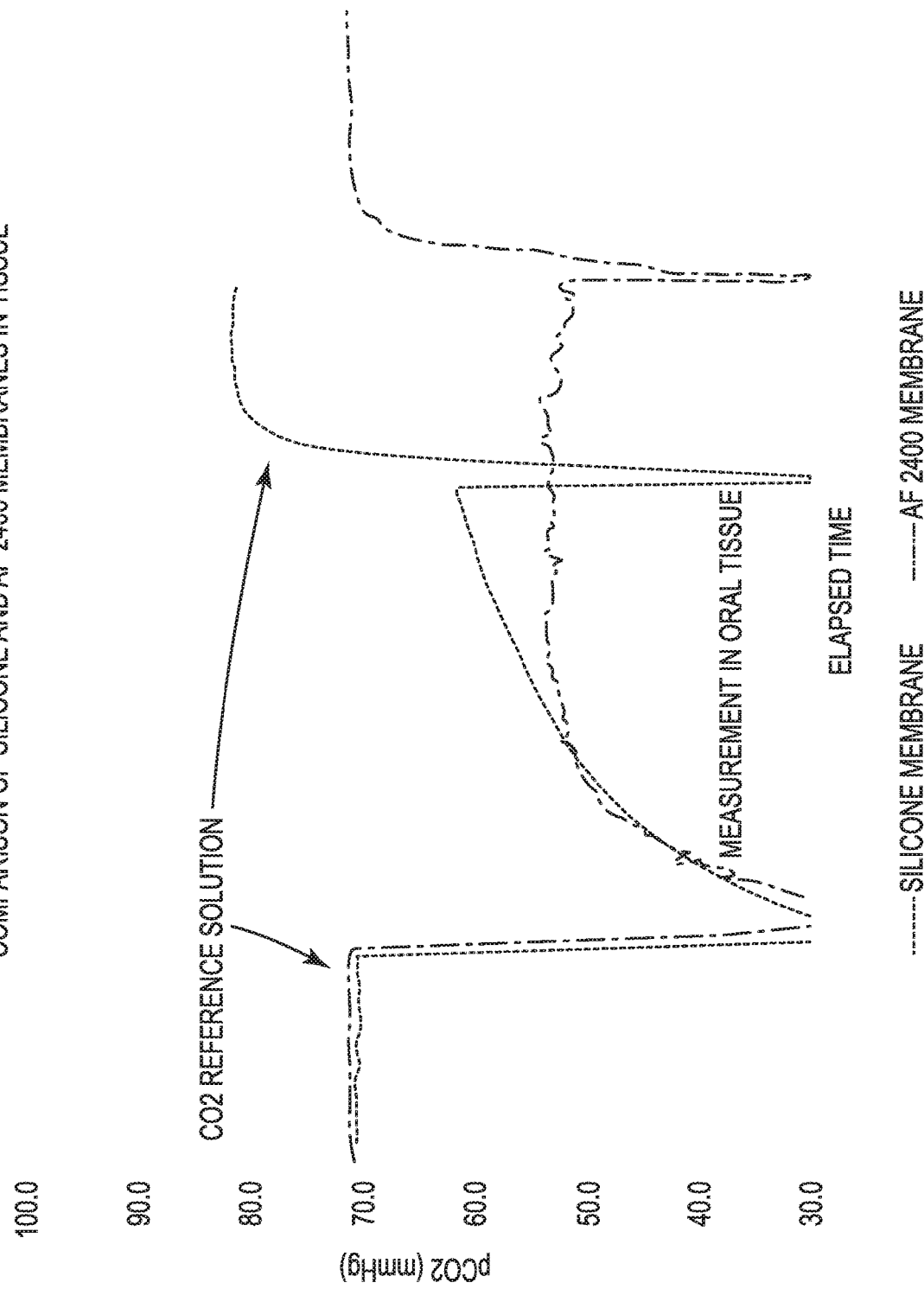
FIG. 9 is a graph illustrating a comparison of silicone and amorphous fluoroplastic membranes in tissue.

Referring now to FIGS. 8 and 9 comparison data will now be discussed. FIG. 8 graphically illustrate the results of an in vitro study of several membrane materials. These membranes were exposed to 8 mM acetic acid solution and the conductance change was monitored in an effort to determine suitability for application in the oral cavity. Membrane thicknesses were chosen based on the ability to achieve a reasonable carbon dioxide permeation rates. The results demonstrate the superiority of the Teflon AF 2400.

FIG. 9 graphically illustrates an overlay of in vivo studies of a sensor constructed with a silicone membrane compared to a sensor constructed with a Teflon AF 2400 membrane. A reference solution was measured pre- and post-exposure to oral mucosal tissue. The results demonstrate the contamination that can occur with the use of a silicone membrane, as well as demonstrating the suitability of Teflon AF 2400.

Although the invention has been described with reference to certain aspects and embodiments, those of skill in the art will appreciate that changes may be made in form and detail without departing from the spirit and scope of the invention.

We claim:

1. A sensor for measuring the partial pressure of carbon dioxide ($pCO_2$) comprising:
  a generally C-shaped in cross-section sensor cover including a lip extending downwardly from a distal end of the sensor cover, the sensor cover defining an opening bounded on a top by an underside of the sensor cover and bounded on a distal end by the lip;
  a cylindrical membrane body housed within the opening the membrane body comprising a first amorphous fluoroplastic, the cylindrical membrane body forming an enclosed chamber including:
    a first end, and
    a second closed end situated against the lip, the second closed end of the cylindrical membrane body sealed with a second amorphous fluoroplastic that has a carbon dioxide transmission rate lower than a carbon dioxide transmission rate of the cylindrical membrane body;
  a sensor body disposed at the first end for coupling the first end to the sensor cover;
  two or more electrodes extending from the first end and positioned within the membrane chamber; and
  a substantially electrolyte-free liquid contained within the membrane chamber and in contact with the two or more electrodes.

2. The sensor of claim 1 wherein the sensor is responsive to an alternating electrical potential to measure the impedance of the substantially electrolyte-free liquid.

3. The sensor of claim 1 wherein the lip of the generally C-shaped in cross-section sensor cover is configured to shield the membrane body from end-tidal carbon dioxide.

4. The sensor of claim 1 wherein the membrane body has a carbon dioxide permeability of 2800 Barrer units.

5. The sensor of claim 1 wherein the first amorphous fluoroplastic is substantially impermeable to low molecular weight carboxylic acids.

6. The sensor of claim 1 further comprising a sensor placement device configured to position the sensor against a buccal surface of a cheek.

7. The sensor of claim 6 wherein the sensor placement device is configured to place the sensor against the buccal surface without air gaps and without applying pressure in excess of 25 mmHg.

8. The sensor of claim 1 wherein the tissue is mucosal tissue.

9. The sensor of claim 8 wherein the tissue is oral mucosal tissue.

10. The sensor of claim 1 wherein the opening is configured to allow tissue contact of the cylindrical membrane body of greater than 40% to 50%.

* * * * *